US008070826B2

(12) United States Patent  
Ginn

(10) Patent No.: US 8,070,826 B2
(45) Date of Patent: *Dec. 6, 2011

(54) NEEDLE APPARATUS FOR CLOSING SEPTAL DEFECTS AND METHODS FOR USING SUCH APPARATUS

(75) Inventor: Richard S. Ginn, San Jose, CA (US)

(73) Assignee: Ovalis, Inc., Mountain View, CA (US)

( * ) Notice: Subject to any disclaimer, the term of this patent is extended or adjusted under 35 U.S.C. 154(b) by 2179 days.

This patent is subject to a terminal disclaimer.

(21) Appl. No.: 10/734,670

(22) Filed: Dec. 11, 2003

(65) Prior Publication Data

US 2004/0127917 A1    Jul. 1, 2004

Related U.S. Application Data

(62) Division of application No. 09/948,453, filed on Sep. 7, 2001, now Pat. No. 6,702,835.

(51) Int. Cl.
*A61F 2/02* (2006.01)
(52) U.S. Cl. .................................................. 623/23.72
(58) Field of Classification Search .................. 606/151, 606/153, 213; 623/23.72
See application file for complete search history.

(56) References Cited

U.S. PATENT DOCUMENTS

| 3,874,388 A | 4/1975 | King et al. |
| 3,875,648 A | 4/1975 | Bone |
| 4,006,747 A | 2/1977 | Kronenthal et al. |
| 4,007,743 A | 2/1977 | Blake |
| 4,576,162 A | 3/1986 | McCorkle |
| 4,601,718 A | 7/1986 | Possis et al. |
| 4,669,473 A | 6/1987 | Richards et al. |
| 4,696,300 A | 9/1987 | Anderson |
| 4,702,250 A | 10/1987 | Ovil et al. |
| 4,705,040 A | 11/1987 | Mueller et al. |
| 4,721,115 A | 1/1988 | Owens |
| 4,741,336 A | 5/1988 | Failla et al. |

(Continued)

FOREIGN PATENT DOCUMENTS

DE    422 22 291 C1    7/1992

(Continued)

OTHER PUBLICATIONS

Ruiz, et al., The Puncture Technique: A New Method for Transcatheter Closure of Patent Foramen Ovale, Catheterization and Cardiovascular Interventions 53:369-372 (2001).

(Continued)

*Primary Examiner* — Melanie Tyson
(74) *Attorney, Agent, or Firm* — Dickstein Shapiro LLP

(57) ABSTRACT

Apparatus and methods for closing a septal defect including a flap of tissue partially detached from a septum of a heart. A needle is advanced through a patient's vasculature within a delivery apparatus until the needle is disposed within a first chamber adjacent the septum. The needle is directed through the flap of tissue until the needle is disposed within a second chamber opposite the septum. A filament attached to an intermediate region of the needle is pulled, thereby causing the needle to pivot about the intermediate region such that the ends of the needle straddle the septal opening. A locking element is secured to the filament to secure the flap of tissue against the septum, and the filament is cut. Alternatively, the filament is biased to coil to engage the flap of tissue and secure the needle against the septum to close the opening.

69 Claims, 4 Drawing Sheets

U.S. PATENT DOCUMENTS

| | | |
|---|---|---|
| 4,800,890 A | 1/1989 | Cramer |
| 4,802,478 A | 2/1989 | Powell |
| 4,836,204 A | 6/1989 | Landymore et al. |
| 4,850,960 A | 7/1989 | Grayzel |
| 4,878,893 A | 11/1989 | Chin |
| 4,892,098 A | 1/1990 | Sauer |
| 4,902,508 A | 2/1990 | Badylak et al. |
| 4,917,089 A | 4/1990 | Sideris |
| 4,929,246 A | 5/1990 | Sinofsky |
| 4,946,467 A | 8/1990 | Ohi et al. |
| 4,985,014 A | 1/1991 | Orejola |
| 4,994,069 A | 2/1991 | Ritchart et al. |
| 5,021,059 A | 6/1991 | Kensey et al. |
| 5,037,433 A | 8/1991 | Wilk et al. |
| 5,041,129 A | 8/1991 | Hayhurst et al. |
| 5,049,153 A | 9/1991 | Nakao et al. |
| 5,073,166 A | 12/1991 | Parks et al. |
| 5,108,420 A | 4/1992 | Marks |
| 5,112,310 A | 5/1992 | Grobe |
| 5,171,218 A | 12/1992 | Fonger et al. |
| 5,171,259 A | 12/1992 | Inoue |
| 5,190,050 A | 3/1993 | Nitzsche |
| 5,190,528 A | 3/1993 | Fonger et al. |
| 5,192,301 A | 3/1993 | Kamiya et al. |
| 5,222,974 A | 6/1993 | Kensey et al. |
| 5,236,440 A | 8/1993 | Hlavacek |
| 5,257,637 A | 11/1993 | El Gazayerli |
| 5,282,827 A | 2/1994 | Kensey et al. |
| 5,284,488 A | 2/1994 | Sideris |
| 5,290,272 A | 3/1994 | Burstein et al. |
| 5,290,278 A | 3/1994 | Anderson |
| 5,300,065 A | 4/1994 | Anderson |
| 5,304,184 A | 4/1994 | Hathaway et al. |
| 5,304,185 A | 4/1994 | Taylor |
| 5,312,341 A | 5/1994 | Turi |
| 5,312,435 A | 5/1994 | Nash et al. |
| 5,318,525 A | 6/1994 | West et al. |
| 5,330,496 A | 7/1994 | Alferness |
| 5,334,191 A | 8/1994 | Poppas et al. |
| 5,334,217 A | 8/1994 | Das |
| 5,357,979 A | 10/1994 | Imran |
| 5,370,679 A | 12/1994 | Atlee, III |
| 5,383,852 A | 1/1995 | Stevens-Wright |
| 5,394,880 A | 3/1995 | Atlee, III |
| 5,403,338 A | 4/1995 | Milo |
| 5,409,469 A | 4/1995 | Schaerf |
| 5,409,481 A | 4/1995 | Poppas et al. |
| 5,413,584 A | 5/1995 | Schulze |
| 5,417,699 A | 5/1995 | Klein et al. |
| 5,417,713 A | 5/1995 | Cohen |
| 5,421,338 A | 6/1995 | Crowley et al. |
| 5,425,744 A | 6/1995 | Fagan et al. |
| 5,431,696 A | 7/1995 | Atlee, III |
| 5,433,727 A | 7/1995 | Sideris |
| 5,441,504 A | 8/1995 | Pohndorf et al. |
| 5,443,478 A | 8/1995 | Purdy |
| 5,451,235 A | 9/1995 | Lock et al. |
| 5,461,235 A | 10/1995 | Cottrell et al. |
| 5,474,573 A | 12/1995 | Hatcher |
| 5,478,353 A | 12/1995 | Yoon |
| 5,486,193 A | 1/1996 | Bourne et al. |
| 5,507,744 A | 4/1996 | Tay et al. |
| 5,507,811 A | 4/1996 | Koike et al. |
| 5,522,873 A | 6/1996 | Jackman et al. |
| 5,527,388 A | 6/1996 | Berke et al. |
| 5,545,138 A | 8/1996 | Fugoso et al. |
| 5,548,872 A | 8/1996 | Oetiker |
| 5,554,162 A | 9/1996 | DeLange |
| 5,570,671 A | 11/1996 | Hickey |
| 5,575,772 A | 11/1996 | Lennox |
| 5,577,299 A | 11/1996 | Thompson et al. |
| 5,578,045 A | 11/1996 | Das |
| 5,582,616 A | 12/1996 | Bolduc et al. |
| 5,584,803 A | 12/1996 | Stevens et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,658,280 A | 8/1997 | Issa |
| 5,662,621 A | 9/1997 | Lafontaine |
| 5,662,643 A | 9/1997 | Kung et al. |
| 5,682,906 A | 11/1997 | Sterman et al. |
| 5,702,368 A | 12/1997 | Stevens et al. |
| 5,702,421 A | 12/1997 | Schneidt |
| 5,709,224 A | 1/1998 | Behl et al. |
| 5,709,707 A | 1/1998 | Lock et al. |
| 5,713,867 A | 2/1998 | Morris |
| 5,713,911 A | 2/1998 | Racenet et al. |
| 5,714,297 A | 2/1998 | Chamberlain et al. |
| 5,716,367 A | 2/1998 | Koike et al. |
| 5,720,754 A | 2/1998 | Middleman et al. |
| 5,722,981 A | 3/1998 | Stevens |
| 5,725,512 A | 3/1998 | Swartz et al. |
| 5,725,552 A | 3/1998 | Kotula et al. |
| 5,725,554 A | 3/1998 | Simon et al. |
| 5,728,151 A | 3/1998 | Garrison et al. |
| 5,733,294 A | 3/1998 | Forber et al. |
| 5,738,652 A | 4/1998 | Boyd et al. |
| 5,741,429 A | 4/1998 | Donadio, III et al. |
| 5,755,778 A | 5/1998 | Kleshinski |
| 5,759,170 A | 6/1998 | Peters |
| 5,769,812 A | 6/1998 | Stevens et al. |
| 5,776,162 A | 7/1998 | Kleshinski |
| 5,782,860 A | 7/1998 | Epstein et al. |
| 5,792,094 A | 8/1998 | Stevens et al. |
| 5,797,960 A | 8/1998 | Stevens et al. |
| 5,807,339 A | 9/1998 | Bostrom et al. |
| 5,810,882 A | 9/1998 | Bolduc et al. |
| 5,810,884 A | 9/1998 | Kiim |
| 5,814,016 A | 9/1998 | Valley et al. |
| 5,814,068 A | 9/1998 | Koike et al. |
| 5,814,097 A | 9/1998 | Sterman et al. |
| 5,823,956 A | 10/1998 | Roth et al. |
| 5,827,216 A | 10/1998 | Igo et al. |
| 5,829,447 A | 11/1998 | Stevens et al. |
| 5,836,311 A | 11/1998 | Borst et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,868,702 A | 2/1999 | Stevens et al. |
| 5,868,733 A | 2/1999 | Ockuly et al. |
| 5,868,753 A | 2/1999 | Schatz |
| 5,879,366 A | 3/1999 | Shaw et al. |
| 5,879,499 A | 3/1999 | Corvi |
| 5,885,238 A | 3/1999 | Stevens et al. |
| 5,893,856 A | 4/1999 | Jacob et al. |
| 5,895,404 A | 4/1999 | Ruiz |
| 5,902,319 A | 5/1999 | Daley |
| 5,904,703 A | 5/1999 | Gilson |
| 5,908,428 A | 6/1999 | Scirica et al. |
| 5,910,150 A | 6/1999 | Saadat |
| 5,913,810 A | 6/1999 | Andre |
| 5,913,842 A | 6/1999 | Boyd et al. |
| 5,919,200 A | 7/1999 | Stambaugh et al. |
| 5,924,424 A | 7/1999 | Stevens et al. |
| 5,927,284 A | 7/1999 | Borst et al. |
| 5,928,181 A | 7/1999 | Coleman et al. |
| 5,928,250 A | 7/1999 | Koike et al. |
| 5,931,848 A | 8/1999 | Saadat |
| 5,941,899 A | 8/1999 | Granger et al. |
| 5,944,738 A | 8/1999 | Amplatz et al. |
| 5,947,997 A | 9/1999 | Pavcnik et al. |
| 5,955,110 A | 9/1999 | Patel et al. |
| 5,967,977 A | 10/1999 | Mullis et al. |
| 5,972,013 A | 10/1999 | Schmidt |
| 5,976,174 A | 11/1999 | Ruiz |
| 5,980,503 A | 11/1999 | Chin |
| 5,989,268 A | 11/1999 | Pugsley, Jr. et al. |
| 5,993,475 A | 11/1999 | Lin et al. |
| 6,007,563 A | 12/1999 | Nash et al. |
| 6,010,517 A | 1/2000 | Baccaro |
| 6,013,052 A | 1/2000 | Durman et al. |
| 6,015,378 A | 1/2000 | Borst et al. |
| 6,024,756 A | 2/2000 | Huebsch et al. |

| Patent No. | Kind | Date | Inventor(s) |
|---|---|---|---|
| 6,027,476 | A | 2/2000 | Sterman et al. |
| 6,030,007 | A | 2/2000 | Bassily et al. |
| 6,036,699 | A | 3/2000 | Andreas et al. |
| 6,036,720 | A | 3/2000 | Abrams et al. |
| 6,056,760 | A | 5/2000 | Koike et al. |
| 6,071,271 | A | 6/2000 | Baker et al. |
| 6,071,292 | A | 6/2000 | Makower et al. |
| 6,077,281 | A | 6/2000 | Das |
| 6,077,291 | A | 6/2000 | Das |
| 6,079,414 | A | 6/2000 | Roth |
| 6,080,182 | A | 6/2000 | Shaw et al. |
| 6,090,084 | A | 7/2000 | Hassett et al. |
| 6,090,096 | A | 7/2000 | St. Goar et al. |
| 6,095,997 | A | 8/2000 | French et al. |
| 6,110,145 | A | 8/2000 | Macoviak |
| 6,113,609 | A | 9/2000 | Adams |
| 6,113,611 | A | 9/2000 | Allen et al. |
| 6,117,159 | A | 9/2000 | Huebsch et al. |
| 6,127,410 | A | 10/2000 | Duhaylongsod |
| 6,132,438 | A | 10/2000 | Fleischman et al. |
| 6,135,981 | A | 10/2000 | Dyke |
| 6,142,975 | A | 11/2000 | Jalisi et al. |
| 6,149,664 | A | 11/2000 | Kurz |
| 6,152,141 | A | 11/2000 | Stevens et al. |
| 6,152,144 | A | 11/2000 | Lesh et al. |
| 6,162,195 | A | 12/2000 | Igo et al. |
| 6,162,202 | A | 12/2000 | Sicurelli et al. |
| 6,165,183 | A | 12/2000 | Kuehn et al. |
| 6,165,204 | A | 12/2000 | Levinson et al. |
| 6,171,329 | B1 | 1/2001 | Shaw et al. |
| 6,174,322 | B1 | 1/2001 | Schneidt |
| 6,187,039 | B1 | 2/2001 | Hiles et al. |
| 6,200,313 | B1 | 3/2001 | Abe et al. |
| 6,206,895 | B1 | 3/2001 | Levinson |
| 6,206,907 | B1 | 3/2001 | Marino et al. |
| 6,214,029 | B1 | 4/2001 | Thill et al. |
| 6,221,092 | B1 | 4/2001 | Koike et al. |
| 6,231,561 | B1 | 5/2001 | Frazier et al. |
| 6,245,080 | B1 | 6/2001 | Levinson |
| 6,254,550 | B1 | 7/2001 | McNamara et al. |
| 6,270,490 | B1 | 8/2001 | Hahnen |
| 6,270,515 | B1 | 8/2001 | Linden et al. |
| 6,275,730 | B1 | 8/2001 | KenKnight et al. |
| 6,277,138 | B1 | 8/2001 | Levinson et al. |
| 6,277,139 | B1 | 8/2001 | Levinson et al. |
| 6,280,432 | B1 | 8/2001 | Turovskiy et al. |
| 6,280,460 | B1 | 8/2001 | Bolduc et al. |
| 6,287,317 | B1 | 9/2001 | Makower et al. |
| 6,290,674 | B1 | 9/2001 | Roue et al. |
| 6,293,920 | B1 | 9/2001 | Sweezer et al. |
| 6,302,903 | B1 | 10/2001 | Mulier et al. |
| 6,305,378 | B1 | 10/2001 | Lesh |
| 6,306,150 | B1 | 10/2001 | Levinson |
| 6,306,424 | B1 | 10/2001 | Vyakarnam et al. |
| 6,309,415 | B1 | 10/2001 | Pulnev et al. |
| 6,312,446 | B1 | 11/2001 | Huebsch et al. |
| 6,319,263 | B1 | 11/2001 | Levinson |
| 6,322,548 | B1 | 11/2001 | Payne et al. |
| 6,328,727 | B1 | 12/2001 | Frazier et al. |
| 6,336,898 | B1 | 1/2002 | Borst et al. |
| 6,342,064 | B1 | 1/2002 | Koike et al. |
| 6,346,074 | B1 | 2/2002 | Roth |
| 6,346,099 | B1 | 2/2002 | Altman |
| 6,346,112 | B2 | 2/2002 | Adams |
| 6,350,229 | B1 | 2/2002 | Borst et al. |
| 6,352,531 | B1 | 3/2002 | O'Conner et al. |
| 6,352,552 | B1 | 3/2002 | Levinson et al. |
| 6,355,052 | B1 | 3/2002 | Neuss et al. |
| 6,364,826 | B1 | 4/2002 | Borst et al. |
| 6,371,906 | B1 | 4/2002 | Borst et al. |
| 6,375,671 | B1 | 4/2002 | Kobayashi et al. |
| 6,379,368 | B1 | 4/2002 | Corcoran et al. |
| 6,387,104 | B1 | 5/2002 | Pugsley, Jr. et al. |
| 6,394,948 | B1 | 5/2002 | Borst et al. |
| 6,398,796 | B2 | 6/2002 | Levinson |
| 6,401,720 | B1 | 6/2002 | Stevens et al. |
| 6,402,772 | B1 | 6/2002 | Amplatz et al. |
| 6,416,493 | B1 | 7/2002 | Del Giglio |
| 6,419,669 | B1 | 7/2002 | Frazier et al. |
| 6,432,059 | B2 | 8/2002 | Hickey |
| 6,436,088 | B2 | 8/2002 | Frazier et al. |
| 6,440,152 | B1 * | 8/2002 | Gainor et al. ............... 606/213 |
| 6,458,100 | B2 | 10/2002 | Roue et al. |
| 6,464,640 | B1 | 10/2002 | Guracar et al. |
| 6,464,645 | B1 | 10/2002 | Park et al. |
| 6,482,224 | B1 | 11/2002 | Michler et al. |
| 6,482,228 | B1 | 11/2002 | Norred |
| 6,485,504 | B1 | 11/2002 | Johnson et al. |
| 6,488,706 | B1 | 12/2002 | Solymar |
| 6,497,698 | B1 | 12/2002 | Fonger |
| 6,506,205 | B2 | 1/2003 | Goldberg et al. |
| 6,532,388 | B1 | 3/2003 | Hill et al. |
| 6,551,272 | B2 | 4/2003 | Gobel |
| 6,551,303 | B1 | 4/2003 | Van Tassel et al. |
| 6,551,344 | B2 | 4/2003 | Thill |
| 6,560,489 | B2 | 5/2003 | Hauck |
| 6,562,052 | B2 | 5/2003 | Nobles et al. |
| 6,572,593 | B1 | 6/2003 | Daum |
| 6,579,259 | B2 | 6/2003 | Stevens et al. |
| 6,585,716 | B2 | 7/2003 | Altman |
| 6,592,552 | B1 | 7/2003 | Schmidt |
| 6,592,557 | B2 | 7/2003 | Barbut |
| 6,596,013 | B2 | 7/2003 | Yang et al. |
| 6,606,513 | B2 | 8/2003 | Lardo et al. |
| 6,613,062 | B1 | 9/2003 | Leckrone et al. |
| 6,623,508 | B2 | 9/2003 | Shaw et al. |
| 6,623,518 | B2 | 9/2003 | Thompson et al. |
| 6,626,841 | B1 | 9/2003 | Atlee, III |
| 6,626,890 | B2 | 9/2003 | Nguyen et al. |
| 6,626,930 | B1 | 9/2003 | Allen et al. |
| 6,629,534 | B1 | 10/2003 | St. Goar et al. |
| 6,632,223 | B1 | 10/2003 | Keane |
| 6,645,225 | B1 * | 11/2003 | Atkinson ............... 606/213 |
| 6,651,672 | B2 | 11/2003 | Roth |
| 6,656,206 | B2 | 12/2003 | Corcoran et al. |
| 6,659,981 | B2 | 12/2003 | Stewart et al. |
| 6,662,045 | B2 | 12/2003 | Zheng et al. |
| 6,663,639 | B1 | 12/2003 | Laufer et al. |
| 6,666,861 | B1 | 12/2003 | Grabek |
| 6,679,268 | B2 | 1/2004 | Stevens et al. |
| 6,685,728 | B2 | 2/2004 | Sinnott et al. |
| 6,689,062 | B1 | 2/2004 | Mesallum |
| 6,692,471 | B2 | 2/2004 | Boudreaux |
| 6,692,512 | B2 | 2/2004 | Jang |
| 6,695,838 | B2 | 2/2004 | Wellman et al. |
| 6,699,231 | B1 | 3/2004 | Sterman et al. |
| 6,702,835 | B2 | 3/2004 | Ginn |
| 6,706,033 | B1 | 3/2004 | Martinez et al. |
| 6,712,804 | B2 | 3/2004 | Roue et al. |
| 6,712,836 | B1 * | 3/2004 | Berg et al. ............... 606/213 |
| 6,726,662 | B2 | 4/2004 | Altman |
| 6,735,471 | B2 | 5/2004 | Hill et al. |
| 6,736,828 | B1 | 5/2004 | Adams et al. |
| 6,746,404 | B2 | 6/2004 | Schwartz |
| 6,749,617 | B1 | 6/2004 | Palasis et al. |
| 6,773,441 | B1 | 8/2004 | Laufer et al. |
| 6,776,784 | B2 | 8/2004 | Ginn |
| 6,776,797 | B1 | 8/2004 | Blom et al. |
| 6,783,499 | B2 | 8/2004 | Schwartz |
| 6,790,218 | B2 | 9/2004 | Jayaraman |
| 6,802,840 | B2 | 10/2004 | Chin et al. |
| 6,821,265 | B1 | 11/2004 | Bertolero et al. |
| 6,840,246 | B2 | 1/2005 | Downing |
| 6,854,467 | B2 | 2/2005 | Boekstegers |
| 6,855,116 | B2 | 2/2005 | Atlee, III |
| 6,866,650 | B2 | 3/2005 | Stevens et al. |
| 6,878,118 | B2 | 4/2005 | Atlee, III |
| 6,882,883 | B2 | 4/2005 | Condie et al. |
| 6,889,694 | B2 | 5/2005 | Hooven |
| 6,899,704 | B2 | 5/2005 | Sterman et al. |
| 6,902,545 | B2 | 6/2005 | Bertolero et al. |
| 6,913,600 | B2 | 7/2005 | Valley et al. |
| 6,915,149 | B2 | 7/2005 | Ben-Haim |
| 6,918,890 | B2 | 7/2005 | Schmidt |
| 6,918,908 | B2 | 7/2005 | Bonner et al. |
| 6,929,011 | B2 | 8/2005 | Knudson et al. |
| 6,932,792 | B1 | 8/2005 | St. Goar et al. |
| 6,932,811 | B2 | 8/2005 | Hooven et al. |

| | | |
|---|---|---|
| 6,934,583 B2 | 8/2005 | Weinberg et al. |
| 6,939,348 B2 | 9/2005 | Malecki et al. |
| 6,939,361 B1 | 9/2005 | Kleshinski |
| 6,952,613 B2 | 10/2005 | Swoyer et al. |
| 6,953,466 B2 | 10/2005 | Palasis et al. |
| 6,955,175 B2 | 10/2005 | Steven et al. |
| 6,960,220 B2 | 11/2005 | Marino et al. |
| 6,971,998 B2 | 12/2005 | Rosenman et al. |
| 6,976,990 B2 | 12/2005 | Mowry |
| 6,991,635 B2 | 1/2006 | Takamoto et al. |
| 6,994,094 B2 | 2/2006 | Schwartz |
| 7,001,415 B2 | 2/2006 | Hooven |
| 7,004,952 B2 | 2/2006 | Nobles et al. |
| 7,018,390 B2 | 3/2006 | Turovskiy et al. |
| 7,020,518 B2 | 3/2006 | Zheng et al. |
| 7,039,467 B2 | 5/2006 | Hauck |
| 7,044,135 B2 | 5/2006 | Lesh |
| 7,048,733 B2 | 5/2006 | Hartley et al. |
| 7,056,331 B2 | 6/2006 | Kaplan et al. |
| 7,083,628 B2 | 8/2006 | Bachman |
| 7,087,072 B2 | 8/2006 | Marino et al. |
| 7,090,683 B2 | 8/2006 | Brock et al. |
| 7,090,686 B2 | 8/2006 | Nobles et al. |
| 7,094,244 B2 | 8/2006 | Schreck |
| 7,097,653 B2 | 8/2006 | Freudenthal et al. |
| 7,101,395 B2 | 9/2006 | Tremulis et al. |
| 7,112,219 B2 | 9/2006 | Vidlund et al. |
| 7,113,831 B2 | 9/2006 | Hooven |
| 7,115,135 B2 | 10/2006 | Corcoran et al. |
| 7,186,251 B2 | 3/2007 | Malecki et al. |
| 7,288,105 B2 * | 10/2007 | Oman et al. ................. 606/215 |
| 2001/0014800 A1 | 8/2001 | Frazier et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0032462 A1 | 3/2002 | Houser et al. |
| 2002/0035374 A1 | 3/2002 | Borillo et al. |
| 2002/0039048 A1 | 4/2002 | Matsuge |
| 2002/0043307 A1 | 4/2002 | Ishida et al. |
| 2002/0052572 A1 | 5/2002 | Franco et al. |
| 2002/0077555 A1 | 6/2002 | Schwartz |
| 2002/0096183 A1 | 7/2002 | Stevens et al. |
| 2002/0099389 A1 | 7/2002 | Michler et al. |
| 2002/0099437 A1 | 7/2002 | Anson et al. |
| 2002/0107531 A1 * | 8/2002 | Schreck et al. ............... 606/142 |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0138095 A1 | 9/2002 | Mazzocchi et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0025421 A1 | 2/2003 | Ebihara et al. |
| 2003/0028213 A1 | 2/2003 | Thill et al. |
| 2003/0033006 A1 | 2/2003 | Phillips et al. |
| 2003/0045893 A1 | 3/2003 | Ginn |
| 2003/0050665 A1 | 3/2003 | Ginn |
| 2003/0059640 A1 | 3/2003 | Marton et al. |
| 2003/0100920 A1 | 5/2003 | Akin et al. |
| 2003/0139819 A1 | 7/2003 | Beer et al. |
| 2003/0144694 A1 | 7/2003 | Chanduszko et al. |
| 2003/0145865 A1 | 8/2003 | Sterman et al. |
| 2003/0167071 A1 | 9/2003 | Martin et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2003/0208232 A1 | 11/2003 | Blaeser et al. |
| 2003/0225421 A1 | 12/2003 | Peavey et al. |
| 2004/0044361 A1 | 3/2004 | Frazier et al. |
| 2004/0073242 A1 | 4/2004 | Chanduszko |
| 2004/0092973 A1 | 5/2004 | Chanduszko et al. |
| 2004/0098042 A1 | 5/2004 | Devellian et al. |
| 2004/0098121 A1 | 5/2004 | Opolski |
| 2004/0133230 A1 | 7/2004 | Carpenter et al. |
| 2004/0133236 A1 | 7/2004 | Chanduszko |
| 2004/0176799 A1 | 9/2004 | Chanduszko et al. |
| 2004/0210301 A1 | 10/2004 | Obermiller |
| 2004/0220596 A1 | 11/2004 | Frazier et al. |
| 2004/0243122 A1 | 12/2004 | Auth et al. |
| 2004/0267191 A1 | 12/2004 | Gifford, III et al. |
| 2004/0267306 A1 | 12/2004 | Blaeser et al. |
| 2005/0034735 A1 | 2/2005 | Deem et al. |
| 2005/0043759 A1 | 2/2005 | Chanduszko |
| 2005/0055050 A1 | 3/2005 | Alfaro |
| 2005/0059984 A1 | 3/2005 | Chanduszko et al. |
| 2005/0070923 A1 | 3/2005 | McIntosh |
| 2005/0080406 A1 | 4/2005 | Malecki et al. |
| 2005/0119675 A1 | 6/2005 | Adams et al. |
| 2005/0125032 A1 | 6/2005 | Whisenant et al. |
| 2005/0131460 A1 | 6/2005 | Gifford, III et al. |
| 2005/0149066 A1 | 7/2005 | Stafford |
| 2005/0149115 A1 | 7/2005 | Roue et al. |
| 2005/0187568 A1 | 8/2005 | Klenk et al. |
| 2005/0187588 A1 | 8/2005 | Stahmann et al. |
| 2005/0187620 A1 | 8/2005 | Pai et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0228434 A1 | 10/2005 | Amplatz et al. |
| 2005/0234509 A1 | 10/2005 | Widomski et al. |
| 2005/0251154 A1 | 11/2005 | Chanduszko et al. |
| 2005/0251201 A1 | 11/2005 | Roue et al. |
| 2005/0256532 A1 | 11/2005 | Nayak et al. |
| 2005/0267495 A1 * | 12/2005 | Ginn et al. |
| 2005/0267523 A1 | 12/2005 | Devellian et al. |
| 2005/0267524 A1 | 12/2005 | Chanduszko |
| 2005/0267525 A1 | 12/2005 | Chanduszko |
| 2005/0267526 A1 | 12/2005 | Wahr et al. |
| 2005/0271631 A1 | 12/2005 | Lee et al. |
| 2005/0273119 A1 | 12/2005 | Widomski et al. |
| 2005/0273124 A1 | 12/2005 | Chanduszko |
| 2005/0273135 A1 | 12/2005 | Chanduszko et al. |
| 2005/0277982 A1 | 12/2005 | Marino et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0015002 A1 | 1/2006 | Moaddeb et al. |
| 2006/0036282 A1 | 2/2006 | Wahr et al. |
| 2006/0036286 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0200197 A1 | 9/2006 | Brenzel et al. |
| 2006/0271089 A1 | 11/2006 | Alejandro et al. |
| 2007/0005018 A1 | 1/2007 | Tekbuchava |
| 2007/0010806 A1 | 1/2007 | Malecki et al. |
| 2007/0049970 A1 | 3/2007 | Belef et al. |
| 2007/0073337 A1 | 3/2007 | Abbott et al. |
| 2007/0123851 A1 | 5/2007 | Alejandro et al. |
| 2007/0185530 A1 | 8/2007 | Chin-Chen et al. |

FOREIGN PATENT DOCUMENTS

| | | |
|---|---|---|
| EP | 0 432 320 A1 | 6/1991 |
| EP | 0 553 259 B1 | 3/1995 |
| EP | 1 013 227 A2 | 6/2000 |
| EP | 1 222 897 A2 | 7/2002 |
| EP | 1 046 375 B1 | 11/2004 |
| WO | WO 92/05828 A1 | 4/1992 |
| WO | WO 92/06733 A1 | 4/1992 |
| WO | WO 96/25179 A1 | 8/1996 |
| WO | WO 96/31157 A1 | 10/1996 |
| WO | WO 97/42878 A1 | 11/1997 |
| WO | WO 98/02100 | 1/1998 |
| WO | WO 98/07375 A1 | 2/1998 |
| WO | WO 99/02100 | 1/1999 |

| | | | |
|---|---|---|---|
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 00/07506 A2 | 2/2000 |
| WO | WO 00/27292 A1 | 5/2000 |
| WO | WO 00/44428 A2 | 8/2000 |
| WO | WO 01/21247 | 3/2001 |
| WO | WO 01/49185 A1 | 7/2001 |
| WO | WO 01/78596 A1 | 10/2001 |
| WO | WO 02/24106 A2 | 3/2002 |
| WO | WO 02/062236 A1 | 8/2002 |
| WO | WO 03/059152 A2 | 7/2003 |
| WO | WO 03/077733 A2 | 9/2003 |
| WO | WO 03/094742 A1 | 11/2003 |
| WO | WO 03/103476 A2 | 12/2003 |
| WO | WO 2004/026146 A1 | 4/2004 |
| WO | WO 2004/043266 A2 | 5/2004 |
| WO | WO 2004/052213 A1 | 6/2004 |
| WO | WO 2004/069055 A2 | 8/2004 |
| WO | WO 2004/086951 A2 | 10/2004 |
| WO | WO 2004/087235 A2 | 10/2004 |
| WO | WO 2005/006990 A2 | 1/2005 |
| WO | WO 2005/027752 A1 | 3/2005 |
| WO | WO 2005/034738 A2 | 4/2005 |
| WO | WO 2005/039419 A1 | 5/2005 |
| WO | WO2005/039419 A1 * | 5/2005 |
| WO | WO 2005/074517 B1 | 8/2005 |
| WO | WO 2005/074814 A2 | 8/2005 |
| WO | WO 2005/082255 A1 | 9/2005 |
| WO | WO 2005/092203 A1 | 10/2005 |
| WO | WO 2005/110240 A1 | 11/2005 |
| WO | WO 2005/112779 A1 | 12/2005 |
| WO | WO 2006/036837 A2 | 4/2006 |

OTHER PUBLICATIONS

U.S. Appl. No. 10/856,493—Amendment and Response, Jan. 7, 2010.
U.S. Appl. No. 10/856,493—Office Action (Severson, R), Oct. 7, 2009.
U.S. Appl. No. 10/856,493—Appeal Brief, Jun. 11, 2009.
U.S. Appl. No. 10/856,493—Office Action (Severson, R), Oct. 28, 2008.
U.S. Appl. No. 10/856,493—Response After Final, Oct. 10, 2008.
U.S. Appl. No. 10/856,493—Office Action (Severson, R), Aug. 11, 2008.
U.S. Appl. No. 10/856,493—Response, Apr. 11, 2008.
U.S. Appl. No. 10/856,493—Office Action (Severson, R), Nov. 21, 2007.
U.S. Appl. No. 10/856,493—Response, Jul. 12, 2007.
U.S. Appl. No. 10/856,493—Office Action (Severson, R), May 30, 2007.
Notice of Allowance, U.S. Appl. No. 10/856,493, Apr. 29, 2010.

* cited by examiner

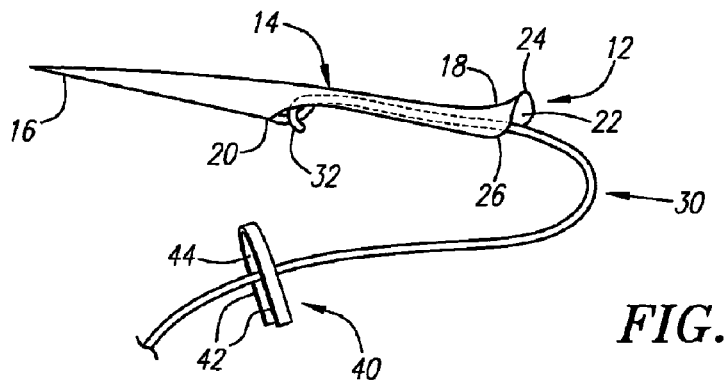
FIG. 1
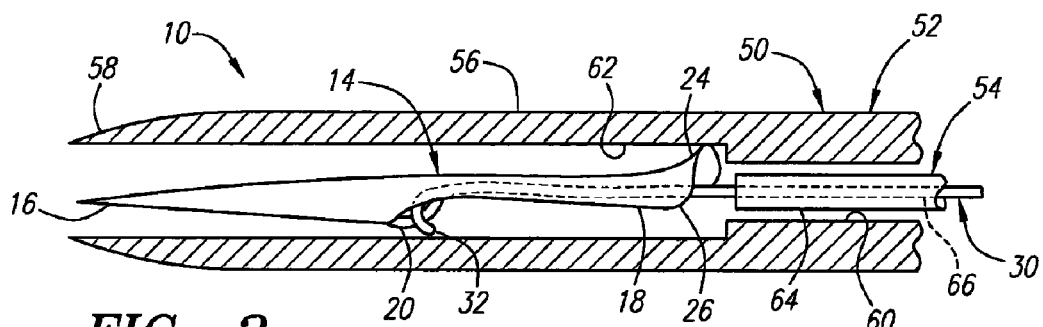
FIG. 2
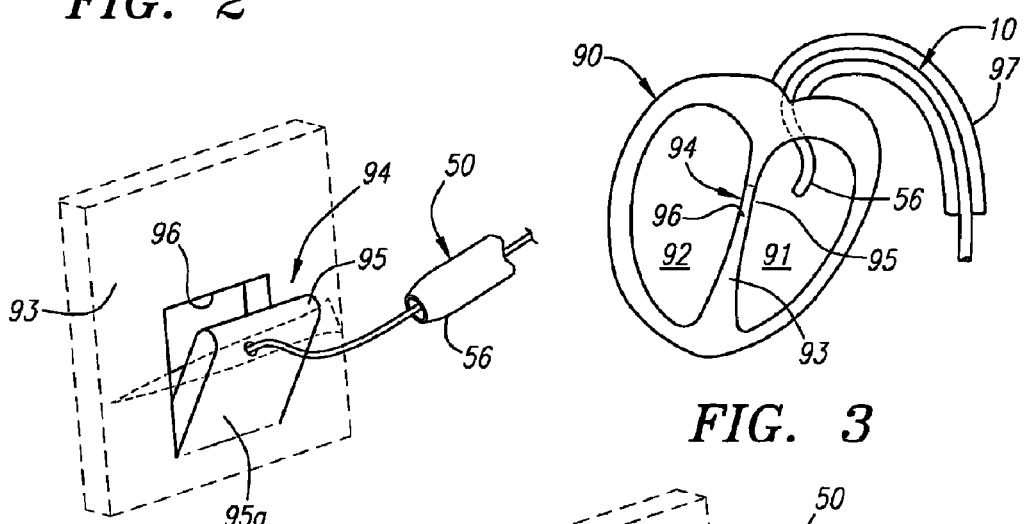
FIG. 3
FIG. 4A
FIG. 4B

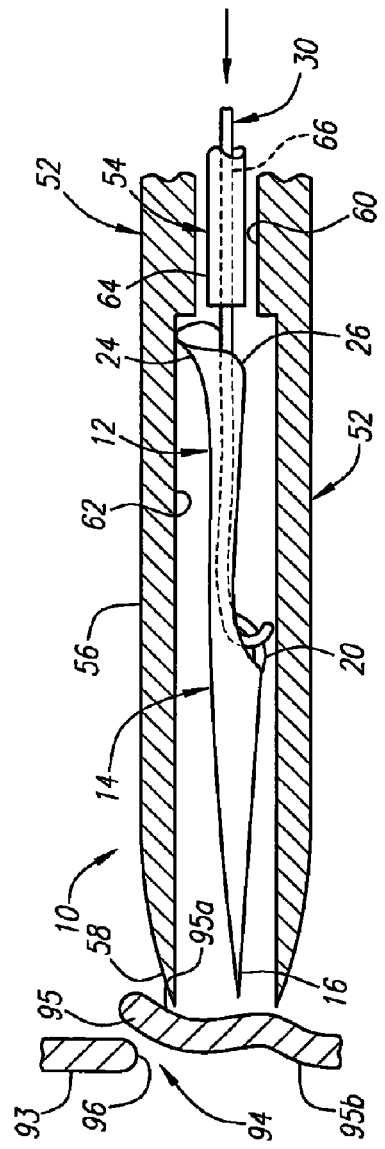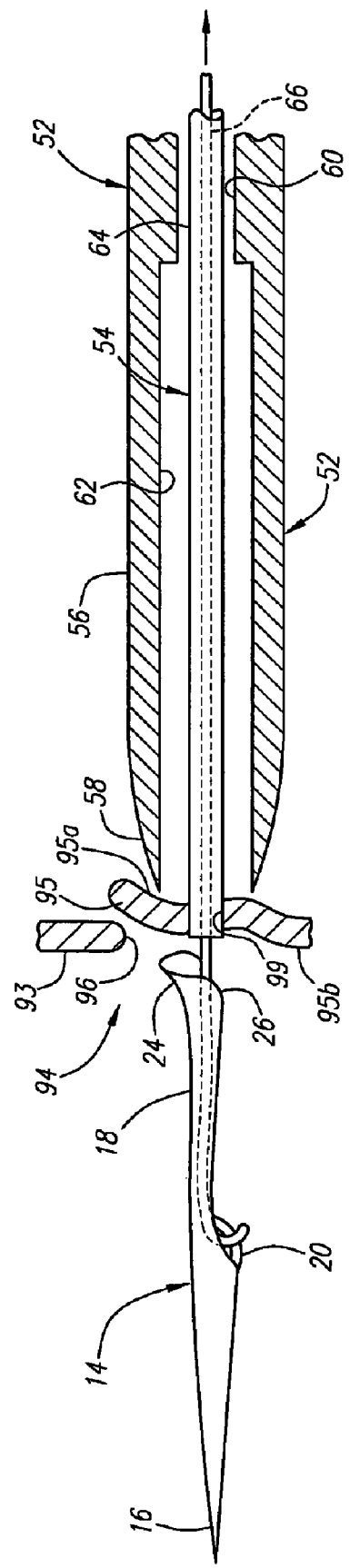

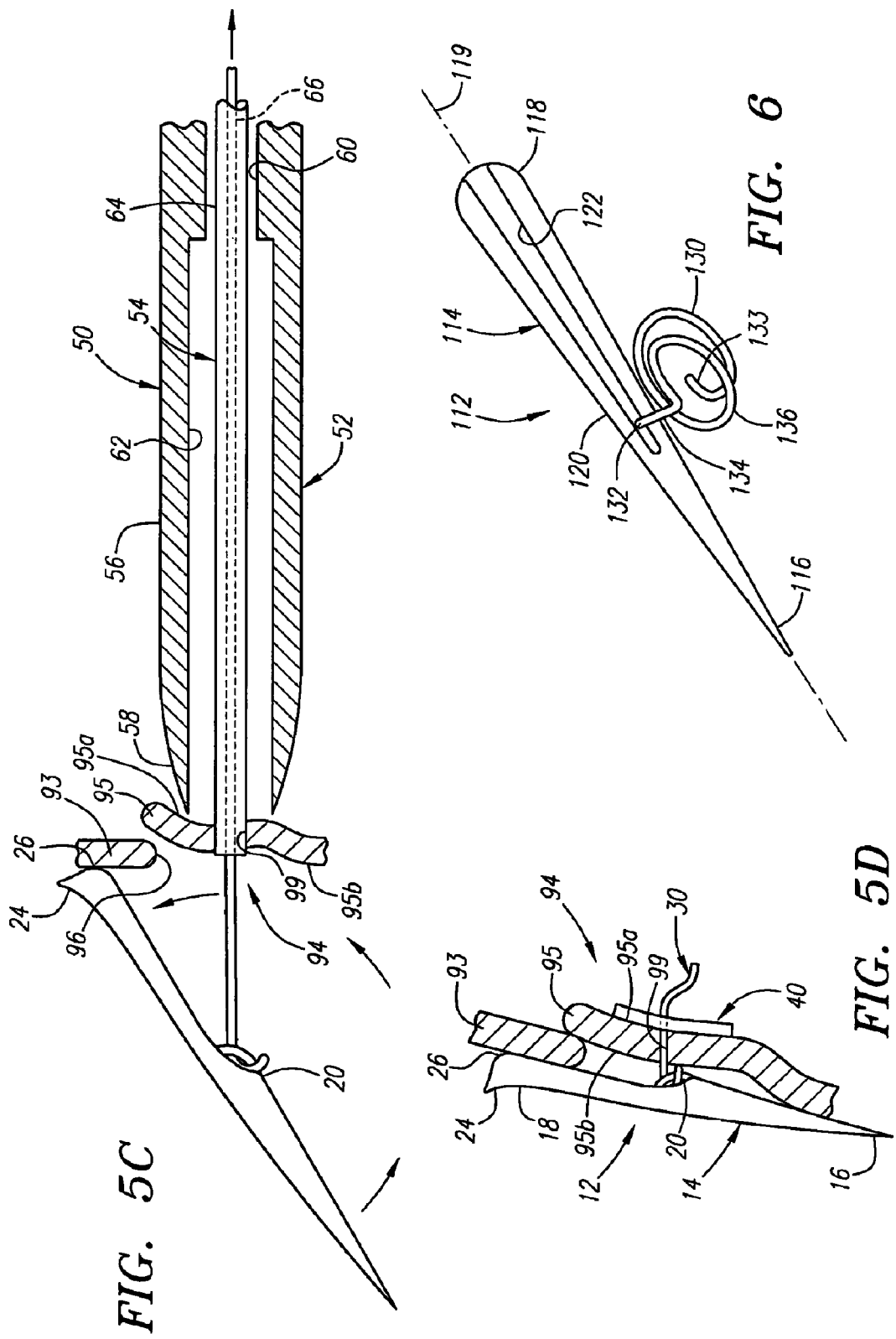

NEEDLE APPARATUS FOR CLOSING SEPTAL DEFECTS AND METHODS FOR USING SUCH APPARATUS

RELATED INFORMATION

This application is a divisional of application Ser. No. 09/948,453 filed on Sep. 7, 2001 now U.S. Pat. No. 6,702,835. The priority of the prior application is expressly claimed, and the disclosure of this application is hereby incorporated by reference in its entirety.

FIELD OF THE INVENTION

The present invention relates generally to apparatus and methods for treating septal defects, and more particularly to apparatus and methods for closing a patent foramen ovale or other septal defect that include a flap of tissue using a needle device.

BACKGROUND

During development of a fetus in utero, blood is generally oxygenated by the mother's placenta, not the fetus' developing lungs. Most of the fetus' circulation is shunted away from the lungs through specialized vessels or foramens that are open during fetal life, but generally close shortly after birth. Occasionally, however, these foramen fail to close and create hemodynamic problems, which may ultimately prove fatal unless treated.

One defect that may occur is a patent foramen ovale ("PFO") or patent ductus arteriosus ("PDA"), which may occur between the left and right atria of the heart. During fetal life, an opening called the foramen ovale allows blood to pass directly from the right atrium to the left atrium (bypassing the lungs). Thus, oxygenated blood from the placenta may travel through the vena cava into the right-atrium, through the foramen ovale into the left atrium, and from there into the left ventricle for delivery via the aorta to the fetus' body. After birth, the foramen ovale is replaced with a membrane called the fossa ovalis, and over time, a solid mass of tissue may form.

Occasionally, this membrane and tissue mass fail to form or completely close the foramen ovale, which may be fatal if untreated. Similar defects may occur in other regions within a septum between chambers of the heart, such as atrial septal defects, ventricular septal defects, and the like.

To close such defects, open surgery may be performed to ligate and close the defect. Such procedures are obviously highly invasive and pose substantial morbidity and mortality risks.

Alternatively, catheter-based procedures have been suggested. These may involve introducing umbrella-like structures into the heart that include opposing expandable structures connected by a hub. One of the expandable structures is inserted through the defect, and both are expanded to secure the tissue surrounding the defect between the structures in an attempt to seal and close the defect. Such structures, however, involve frame structures that support membranes, both of which may fail during the life of the patient being treated, opening the defect, and/or releasing segments of the structure within the patient's heart.

Accordingly, apparatus and methods for closing patent foramen ovale, patent ductus arteriosus, or other septal defects would be considered useful.

SUMMARY OF THE INVENTION

The present invention is directed to apparatus and methods for closing patent foramen ovale ("PFO"), patent ductus arteriosus ("PDA"), or other septal defects.

In accordance with a first aspect of the present invention, an apparatus for closing a septal defect is provided that includes an elongate needle including a first end defining a tissue-penetrating tip, and a second end defining a substantially blunt tip. A filament extends from an intermediate portion of the needle between the first and second ends, and a locking element, such as a clip, clamp, cross-brace, and the like, may be securable to the filament, thereby preventing the locking element from moving along the filament away from the needle.

Preferably, the needle has a tapered cross-section such that the second end is substantially larger than the first end. A slot may be provided in the needle that extends from the intermediate portion to the second end, the slot having a size for receiving a portion of the filament therein. The second end of the needle may include a flared outer edge and/or a rounded inner edge.

In one embodiment, the locking element may be a clip that is slidable along the filament towards the needle, the clip including opposing arms having teeth or other engaging elements for preventing the clip from being moved along the filament away from the needle. Alternatively, the clip may be plastically deformable such that the clip may received around the filament and then crimped or otherwise secured to the filament during closure of a septal defect, as explained further below.

In accordance with another aspect of the present invention, a delivery apparatus for delivering a needle apparatus, such as that described above, is provided that includes an outer catheter and a pusher member that are slidably coupled to one another. The catheter may be a tubular member including proximal and distal ends and a lumen therebetween, the distal end having a size for insertion into a blood vessel or other body lumen. The needle may be carried within the lumen such that the first end is disposed distally to the second end.

The pusher member may be an inner catheter or other elongate member that is disposed within the lumen of the outer catheter. The pusher member may include a distal end that may be disposed proximate the second end of the needle, the pusher member being movable axially relative to the tubular member for ejecting the needle distally from the lumen. The pusher member may include a lumen extending proximally from the distal end of the pusher member such that the filament extending from the needle may be received through the lumen.

An actuator may be provided on the proximal end of the tubular member and/or the pusher member for advancing the pusher member relative to the tubular member. Preferably, the actuator may-limit advancement of the pusher member such that the distal end of the pusher member extends only a predetermined distance beyond the distal end of the tubular member when activated. The actuator may also be coupled to the filament received through the lumen in the pusher member for applying proximal tension to the filament during use, as described further below.

The lumen of the catheter may include an enlarged distal region proximate the distal end for receiving the needle therein. For example, the second end of the needle may have a cross-section that is substantially larger than a cross-section of the distal end of the pusher member. In addition, the second end of the needle may have a flared outer edge such that the second end extends laterally from the distal end of the pusher member. Alternatively, the second end of the needle may simply be larger in cross-section than the distal end of the pusher member, In addition, the second end of the needle may include a rounded edge for facilitating pivoting of the needle about the intermediate region when the filament is pulled proximally.

In addition, the delivery apparatus may include a clip carrier having a proximal end and a distal end having a size for introduction into a body lumen. A clip or other locking element may be releasably carried by the distal end of the clip carrier, the clip including opposing arms defining a slot therebetween for receiving a filament therein. The clip carrier may include a hammer/anvil arrangement-for plastically deforming at least one of the opposing arms to engage a filament received within the slot. The clip carrier may be completely separate from the catheter and pusher member or may be carried by the catheter and/or pusher member. For example, the catheter may include an additional lumen through which the clip carrier may be advanced.

In a further alternative, the delivery apparatus may include an imaging device including an imaging element associated with the distal end of the tubular member for imaging beyond the distal end of the tubular member. For example, the imaging device may be an endoscope or ultrasound device that may be received within a lumen of the tubular member or may be a separate device that may introduced independently into the patient but used in conjunction with the delivery apparatus during a procedure.

In accordance with yet another aspect of the present invention, a method is provided for closing a PFO or other septal defect within a patient's heart. Generally, the septal defect includes a flap of tissue partially detached from a septum wall between first and second chambers of the heart, the flap of tissue and surrounding tissue of the septum wall defining a septal opening through the septum wall. Initially, a needle may be provided that includes a first end defining a tissue-penetrating tip, a second end defining a substantially blunt tip, and an intermediate portion between the first and second ends from which a filament extends.

The needle may be advanced through the patient's vasculature until the needle is disposed within the first chamber of the heart adjacent the septal opening. For example, the needle may be disposed within a distal end of a delivery apparatus including a catheter and a pusher member slidably coupled to one another. The distal end of the delivery apparatus may be advanced through the patient's vasculature, e.g., from a percutaneous entry site, into the first chamber until the distal end is disposed adjacent the flap of tissue.

The first end of the needle may be directed through the flap of tissue until the second end passes through the flap of tissue and the needle is disposed within the second chamber of the heart. For example, the pusher member may be advanced distally relative to the catheter, thereby directing the needle from within the delivery apparatus and into and through the flap of tissue. Preferably, the pusher member is advanced a predetermined distance, e.g., such that the distal end of the pusher member extends completely through the flap of tissue to ensure that the needle is directed entirely into the second chamber.

The filament may then be pulled proximally, thereby causing the needle to pivot about the intermediate region such that the first and second ends of the needle straddle the septal opening within the second chamber. As the filament is pulled, the blunt tip of the needle may engage a distal surface of the flap of tissue, thereby preventing the needle from being pulled back through the flap of tissue. The blunt tip of the needle may include an enlarged or flared end, e.g., larger than the distal end of the pusher member, also to prevent the needle from being pulled through the flap of tissue. Instead, the blunt tip of the needle may slide along a distal surface of the flap of tissue and/or the septum wall, thereby causing the needle to pivot about the intermediate region of the needle. Preferably, the blunt tip of the needle includes a rounded inner edge for facilitating movement of the needle along the distal surface.

The flap of tissue may be directed into engagement with the septum wall to at least partially close the septal opening. For example, a locking element may be secured to the filament, the locking element engaging the proximal surface of the flap of tissue to secure the flap of tissue between the needle and the locking element. To accomplish this, a clip carrier may be introduced into the first chamber of the heart. The clip carrier may be manipulated to receive the filament within a clip carried by the clip carrier, and then the clip may be crimped or otherwise plastically deformed, e.g., by a mechanical crimper on the clip carrier, to secure the clip to the filament. Alternatively, a locking element may be slidably secured on the filament. The locking element may be slid along the filament towards the needle until the flap of tissue is secured against the tissue surrounding the septal opening. The locking element may include teeth or other elements that accommodate sliding the locking element along the filament towards the needle, but prevent subsequent movement of the locking element along the filament away from the needle. In addition, the needle and/or locking element may have lengths greater than a width of the septal opening, such that the flap of tissue may be secured between the needle and the locking element, thereby substantially closing the septal opening. The filament may be cut or otherwise detached from the delivery apparatus, and the delivery apparatus removed from the patient's body.

In accordance with still another aspect of the present invention, an apparatus is provided that includes an elongate needle including a first end defining a tissue-penetrating tip, a second end defining a substantially blunt tip, and a longitudinal axis extending between the first and second ends. A filament extends from an intermediate portion of the needle between the first and second ends. At least a segment of the filament may be biased towards a configuration defining a plane extending generally parallel to the longitudinal axis. Thus, the filament may be extendable towards a generally linear configuration, but may resiliently attempt to return towards the planar configuration.

In a preferred embodiment, the filament includes first and second segments. The first segment may be attached to the intermediate portion of the needle and biased to extend transversely with respect to the longitudinal axis. The second segment extends from the first segment and may be biased to extend transversely to the first segment such that the second segment defines the plane that extends generally parallel to the longitudinal axis of the needle. The second segment may be biased towards a coiled configuration, the coiled configuration lying substantially within the plane. Alternatively, the second segment may be biased towards other planar configurations lying substantially within the plane, for example, including at least one of an "L," a "U," a "Y," and/or an "S" shape.

The apparatus may include a tubular member, including proximal and distal ends and a lumen extending therebetween. The distal end may have a size for insertion into a blood vessel. Generally, the needle is carried within the lumen such that the first end is disposed distally to the second end. A pusher member may be slidably disposed within the lumen, the pusher member including a distal end disposed proximate the second end of the needle. Preferably, the pusher member is movable axially relative to the tubular member for ejecting the needle distally from the lumen.

The pusher member and/or the tubular member may include a gripping mechanism for releasably securing a loose end of the filament, thereby restraining the filament in the generally linear configuration. An actuator may also be provided on the proximal end of the pusher member and/or the tubular member for releasing the loose end of the filament, whereupon the filament may be free to assume the planar configuration.

The apparatus may be used for closing a septal defect within a patient's heart, similar to the embodiment described above. The needle may be advanced through the patient's vasculature, e.g., within the tubular member, until the needle is disposed within the first chamber of the heart adjacent the septal opening. The first end of the needle may be directed through the flap of tissue until the second end passes through the flap of tissue and the needle is disposed within the second chamber of the heart. The filament may be pulled, thereby causing the needle to pivot about the intermediate region such that the first and second ends of the needle straddle the septal opening within the second chamber. The filament may then be released, the filament resiliently assuming a generally planar configuration, thereby engaging the flap of tissue between the needle and the filament to at least partially close the septal opening.

Other objects and features of the present invention will become apparent from consideration of the following description taken in conjunction with the accompanying drawings.

BRIEF DESCRIPTION OF THE DRAWINGS

FIG. 1 is a perspective view of a first preferred embodiment of a needle apparatus for closing a septal defect, in accordance with the present invention.

FIG. 2 is a cross-sectional side view of a delivery apparatus for delivering the needle apparatus of FIG. 1.

FIG. 3 is a cross-sectional view of a heart including a PFO in a septum wall of the heart, showing an apparatus being introduced for treating the PFO.

FIGS. 4A and 4B are perspective details of the PFO of FIG. 3, showing a method for closing a PFO using the needle apparatus of FIG. 1.

FIGS. 5A-5D are cross-sectional views, showing a method for closing a PFO using the needle apparatus of FIG. 1.

FIG. 6 is a perspective view of a second preferred embodiment of a needle apparatus for closing a septal defect, in accordance with the present invention.

DETAILED DESCRIPTION OF THE PREFERRED EMBODIMENTS

Figure 7:
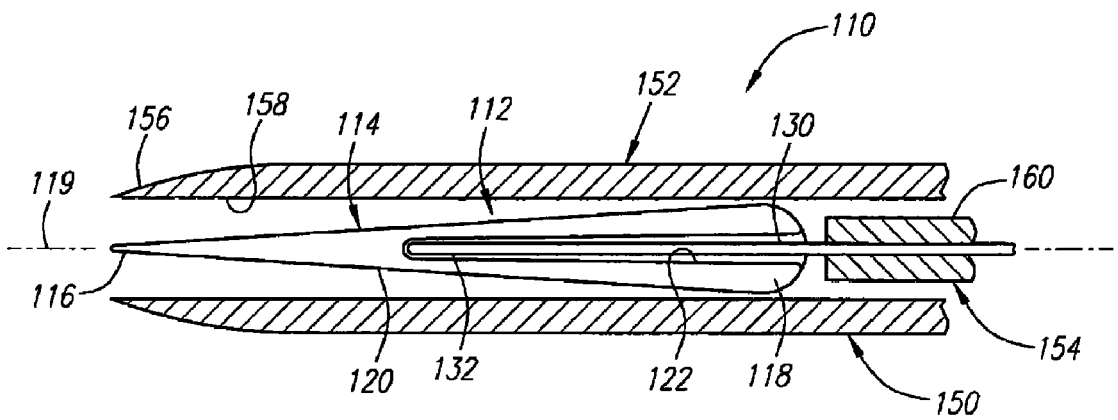
FIG. 7 is a cross-sectional side view of an apparatus for delivering the needle apparatus of FIG. 6.

Turning now to the drawings, FIGS. 1 and 2 show a first preferred embodiment of an apparatus 10 for closing a septal defect, such as a PFO or PDA, in accordance with the present invention. Generally, the apparatus 10 includes a needle apparatus 12 and a delivery apparatus 50 for introducing and deploying the needle apparatus 12.

With particular reference to FIG. 1, the needle apparatus 12 includes an elongate needle 14 including a first end 16 defining a tissue-penetrating tip, a second end 18 defining a substantially blunt tip, and an intermediate region 20 between the first and second ends 16, 18. The needle 14 may be formed from a variety of substantially rigid biocompatible materials, e.g., stainless steel.

Preferably, the needle 14 includes a longitudinal slot 22 therein that extends between the intermediate region 20 and the second end 18. The second end 18 of the needle 14 may include a flared outer edge 24 that extends transversely outwardly, and a rounded inner edge 26. The second end 18 of the needle 14 preferably has a cross-section that is substantially larger than the first end 16, and more preferably that is substantially larger than the intermediate region 20. For example, the second end 18 may have a generally "U" shape, as shown, defining the slot 22 therein.

The needle apparatus 12 also includes a filament 30 that extends from the intermediate region 20 of the needle 14. The filament 30 is preferably formed from a substantially inelastic biocompatible material, such as non-bioabsorbable suture material, e.g., plastic. Preferably, a first end 32 of the filament 30 is substantially permanently attached to the intermediate region 20, e.g., through a loop 34 on the intermediate region 20, and a second end (not shown) of the filament 30 is loose. Alternatively, a wall of the intermediate region 20 may include a hole (not shown) through which the first end 32 of the filament 30 may be secured. In a further alternative, the intermediate region 20 may include a recess, groove, slot, and the like (not shown), for receiving the first end 32, e.g., such that the filament 30 may be tied around the intermediate region 20 and received within the recess. In addition or alternatively, the first end 32 of the filament 30 may be attached to the needle 14 by an adhesive or other bonding method, sonic welding, and the like.

In addition, the needle apparatus 12 may also include a clip or other locking element 40 that may be secured to the filament 30. In a preferred embodiment, the clip 40 includes opposing arms 42 defining a slot 44 therebetween for receiving the filament 30 therein. The inner surfaces of the arms 42 may include teeth or other engaging elements (not shown) that allow the clip 40 to be directed along the filament 30 towards the needle 12, but prevent the clip 40 from being moved along the filament 30 away from the needle 12. Alternatively, the clip 40 may be plastically deformable such that the arms 42 may be disposed initially apart sufficient to freely introduce the filament 30 therebetween, and then crimped or otherwise directed towards one another to frictionally secure the clip 40 at a desired location on the filament 30.

With particular reference to FIG. 2, the delivery apparatus 50 generally includes an outer catheter or tubular member 52, and an inner catheter or pusher member 54. The outer catheter 52 includes a proximal end (not shown), and a distal end 56 having a size for insertion into a blood vessel or other body lumen (not shown). The distal end 56 preferably has a tapered and/or rounded distal tip 58, e.g., for facilitating substantial atraumatic advancement of the delivery apparatus 50 through a patient's vasculature. The outer catheter 52 also includes a lumen 60 therein that extends between the proximal and distal ends 56. In the embodiment shown, the lumen 60 includes an enlarged distal region 62 having a size for receiving the needle 12. Preferably, the needle 14 may be received in the enlarged distal region 62 such that the first end 16 is disposed distally to the second end 18 therein.

The pusher member 54 includes a proximal end (not shown) and a distal end 64 having a size such that the pusher member 54 may be slidably disposed within the lumen 60 of the outer catheter 52. The distal end 64 is preferably substantially blunt and has a cross-section that is substantially smaller than a projected cross-section of the needle 12. The distal end 64 is disposed proximate the second end 18 of the needle 12, and the pusher member 54 is movable axially relative to the outer catheter 52 for ejecting the needle 12 distally from the lumen 60, as described further below. In a preferred embodiment, the pusher member 54 includes a lumen 66 extending proximally from the distal end 64 of the pusher member 54, and preferably extending to the proximal end of the pusher member 54. As shown, the lumen 66 has a size for receiving the filament 30 therethrough.

Alternatively, the pusher member 54 may include a longitudinal groove or slot (not shown) extending along an outer wall of the pusher member 54 from the distal end 64 to the proximal end. The groove or slot may have a size for slidably receiving the filament 309 therein. In a further alternative, the delivery apparatus may include interlocked rails (not shown) that may slide axially relative to one another in a controlled manner, instead of the outer catheter 52 and the pusher member 54.

An actuator, e.g., a handle device (not shown), may be provided on the proximal end of the outer catheter 52 and/or the pusher member 54 that may limit relative axial movement of the outer catheter 52, the pusher member 54, and/or the filament 30. For example, the actuator may be fixed to the outer catheter 52 and coupled to the pusher member 54 for advancing the pusher member 54 relative to the outer catheter 52 (or alternatively, for retracting the outer catheter 52 relative to the pusher member 54). Preferably, the actuator allows advancement of the pusher member 54 such that the distal end 64 of the pusher member 54 extends a predetermined distance beyond the distal tip 58 of the outer catheter 52 and then prevents further distal advancement. In addition, the actuator may be coupled to the second end of the filament 30, e.g., for pulling the filament proximally relative to the outer catheter 52 and/or pusher member 54, as described further below.

Use of the apparatus 10 for closing a septal defect 94 is shown in conjunction with FIGS. 3-5D. FIG. 3 generally shows a heart 90 of a patient, including heart chambers 91, 92 separated by a septum wall 93. The septal defect 94, such as a PFO or PDA, is shown in the septum wall 93, which may be located in the septum wall between the right atrium and the left atrium of the heart. As best seen in FIGS. 4A-5D, the septal defect 94 may include a flap of tissue 95 that is at least partially detached from the septum wall 93, thereby defining an opening 96 in the septum wall 93. Alternatively, the septal defect may be an opening that extends through the septum wall 93, e.g., laterally such that the septal defect includes flaps of tissue that partially overlap one another (not shown).

The apparatus 10, i.e., the delivery apparatus 50 with the needle apparatus 12 therein (the latter not shown in FIG. 3, see FIGS. 5A-5D), may be introduced into the patient's vasculature, e.g., from a percutaneous entry site in a peripheral vessel, such as the femoral artery, carotid artery, and the like (not shown). The apparatus 10 may be advanced endoluminally within the patient's vasculature, e.g., through the aortic arch 97 and into the heart 90 until the distal end 56 is disposed within the chamber 91, which is shown in FIG. 3 to be the left atrium. Preferably, access into the heart 90 may be obtained using a venous approach. The apparatus 10 may be introduced percutaneously into a peripheral vein, such as the femoral or jugular vein, and advanced through the vena cava (not shown) into the right atrium.

With particular reference to FIGS. 5A-5D, the distal end 56 of the apparatus 10 may be advanced into contact with a proximal surface 95a of the flap of tissue 95, e.g., such that the flap of tissue 95 is disposed proximate the septal opening 96, as shown in FIG. 5A (e.g., within the right atrium, not shown). The pusher member 54 may be advanced distally relative to the outer catheter 52, thereby piercing the first end 16 of the needle 14 through the flap of tissue 95 until the needle 14 enters the chamber 92 beyond the septum wall 93 (e.g., the left atrium, not shown), thereby creating a puncture 99. Preferably, the penetrating tip on the first end 16 of the needle 14 is substantially sharp to facilitate piercing and passing through the flap of tissue 95. The substantially blunt tip on the second end 18 of the needle 14 enhances engagement with the distal end 64 of the pusher member 54 to facilitate pushing the needle 14 through the flap of tissue 95 to create the puncture 99.

Preferably, the pusher member 54 is advanced distally until the second end 18 of the needle 14 passes entirely through the flap of tissue 95, as shown in FIG. 5B. For example, the actuator (not shown) on the delivery apparatus 50 may allow controlled advancement of the pusher member 54 to allow the distal end 64 of pusher member 54 to be disposed a predetermined distance beyond the distal tip 58 of the outer catheter 52. Preferably, the predetermined distance is a distance greater than a thickness of the flap of tissue 95, e.g., at least about two to ten millimeters (2-10 mm), such that the distal end 64 of the pusher member 54 passes through the puncture 99, thereby ensuring that the second end 18 of the needle 14 is advanced completely beyond the distal surface 95b of the flap of tissue 95.

The pusher member 54 may then be retracted proximally, e.g., to withdraw the distal end 58 back through the flap of tissue 95 and at least partially into the lumen 60 of the outer catheter 52. The filament 30 may be pulled proximally, either before or after retraction of the pusher member 54, thereby causing the second end 18 of the needle 14 to engage the distal surface 95b of the flap of tissue 95. Because of the substantially blunt tip on the second end 18, the needle 14 may not pass back through the puncture. Preferably, because of the flared outer edge 24, the second end 18 of the needle 14 is offset laterally relative to the distal end 64 of the pusher member 54, thereby preventing the second end 18 from following the pusher member 54 back through the puncture 99. Thus, the second end 18 engages the distal surface 95b and retains the needle 14 entirely within the chamber 92.

With particular reference to FIG. 5C, because the filament 30 is coupled to the intermediate region 20 of the needle 14, continued pulling of the filament 30 proximally may cause the needle 14 to pivot about the intermediate region 20. Preferably, the rounded inner edge 26 allows the second end 18 of the needle 14 to slide and pivot along the distal surface 95b of the flap of tissue 95 and/or along the septum wall 93. As the filament 30 is pulled further, the needle 14 is directly substantially transversely, and preferably substantially parallel to the septum wall 93, e.g., until it abuts the distal surface 95b of the flap of tissue 95 and/or the septum wall 93, as best seen in FIGS. 4A and 5C. Preferably, a length of the needle 14 is substantially longer than a width of the opening 96 such that the first and second ends 16, 18 of the needle 14 straddle the opening 96 and engage the septum wall 93 on either side of the septal defect 94.

As best seen in FIGS. 4B and 5D, the clip 40 may then be secured to the filament 30 such that the clip 40 substantially abuts the proximal surface 95a of the flap of tissue 95. For example, in one embodiment, the clip 40 may be provided within the lumen of the outer catheter 54 and advanced along the filament 30 towards the needle 14 until the clip 54 contacts the proximal surface 95a. As the clip 40 is directed further distally, the flap of tissue 95 is forced into contact with the septum wall 93 surrounding the opening 96, possible even filling the opening 96, as shown in FIG. 4B.

Alternatively, the clip 40 may be carried by a separate device (not shown) than the delivery apparatus 50. For example, a clip carrier (not shown) may be introduced into the chamber 91, e.g., from a percutaneous entry site (not shown), and advanced endoluminally into the chamber 92. In a further alternative, the outer catheter 52 of the delivery apparatus 50 may include an additional lumen (not shown) from which a clip carrier may be advanced.

The clip 40 may be directed around the filament 30 and secured within the slot of the filament 30. For example, the clip carrier may include a hammer-anvil arrangement (not shown) that may be used to crimp or otherwise plastically deform the clip 40 to substantially engage the filament 30. Preferably, tension is applied to the filament 30, and the clip 40 is brought into close proximity with the proximal surface 95a of the flap of tissue 95 before the clip 40 is crimped, thereby securing the clip 40 against the flap of tissue 95.

Alternatively, the clip 40 may be slidably received on the filament 30, e.g., by a separate clip carrier (not shown) or may be provided on the filament 30 within the delivery apparatus 50 (also not shown). One or more tools may be used to apply proximal tension to the filament 30 and drive the clip 40 distally towards the needle 14, e.g., until the clip 40 engages the flap of tissue 95.

This arrangement of needle apparatus 12 may be used for a flap of tissue 95 that falls proximally away from the opening 96 in the septum wall 93 (into the proximal chamber 91 shown in FIG. 3). As the clip 40 is advanced distally over the filament 30, the first and second ends 16, 18 of the needle 14 may provide anchors such that the clip 40 may push the flap of tissue 95 into the opening 96 and/or into contact with the surrounding septum wall 93.

Alternatively, if the flap of tissue 95 falls distally away from the opening 96 (not shown), the filament 30 may be pulled proximally in order to cause the needle 14 to direct the flap of tissue 95 into contact with the septum wall 93 surrounding the opening 96 and/or to substantially fill the opening 96. To hold the flap of tissue 95 in this closed position, a clip (not shown) may be advanced over the filament 30 or otherwise secured to the filament 30. Preferably, the clip has a length or cross-section that is greater than the cross-section of the opening 96 such that the clip abuts the septum wall 93 surrounding the opening 96. Thus, the flap of tissue 95 may be sandwiched between the needle 14 and the clip, which engage opposing surfaces of the surrounding septum wall in order to secure the flap of tissue 95 substantially closed.

Once the needle 14, clip 40, and flap of tissue 95 are secured as desired, the filament 30 may be cut and the delivery apparatus 50 removed from the patient's body. For example, the clip carrier may include a cutting element (not shown) that may be used to cut the filament at a location close to the clip 40, as shown in FIGS. 4B and 5D. The cutting element may simply be a blade, scissors, and the like that is deployable from the clip carrier. Alternatively, a cutting element may be advanced through a lumen (not shown) in the outer catheter 52, or may be a separate device that may be introduced independently through the patient's vasculature into the chamber 92 of the heart 90.

It will be appreciate by those skilled in the art that the procedure described herein may be monitored in a variety of ways. For example, the delivery apparatus 50 may include an imaging device, such as an endoscope or other fiber optic device, an intravascular ultrasound ("IVUS") device, and the like (not shown). The device may be provided on the distal end 56 of the outer catheter 52, e.g., attached to or adjacent the distal tip 58 or advanceable from a lumen (not shown) therein. In a further alternative, external imaging may be used, either alone or in conjunction with direct visualization. For example, the needle 14, the clip 40, the outer catheter 52, and/or the pusher member 54 may include radiopaque markers (not shown) at predetermined locations that may be observed using fluoroscopy and the like.

Turning to FIGS. 6 and 7, another preferred embodiment of an apparatus 110 is shown for closing a septal defect, such as a PFO or PDA, that generally includes a needle apparatus 112 and a delivery apparatus 150 for introducing and deploying the needle apparatus 112.

With particular reference to FIG. 6, the needle apparatus 112 includes an elongate needle 114 including a first end 116 defining a tissue-penetrating tip, a second end 118 defining a substantially blunt or rounded tip, and a longitudinal axis 119 between the first and second ends 116, 118. The needle 114 may be formed from a variety of substantially rigid biocompatible materials, e.g., stainless steel.

Preferably, the needle 114 includes a longitudinal slot 122 therein that extends between an intermediate region 120 of the needle 114 and the second end 118. The second end 118 of the needle 114 may include a flared outer edge and/or a rounded inner edge (not shown), similar to the previous embodiment. The second end 118 of the needle 114 preferably has a cross-section that is substantially larger than the first end 116, and more preferably that is substantially larger than the intermediate region 120. For example, the second end 118 may have a generally "U" shape, as shown, defining the slot 122 between edges 123.

The needle apparatus 112 also includes a filament 130 that extends from the intermediate region 120 of the needle 114. The filament 130 may be formed from a superelastic and/or shape memory material, such as Nitinol. Preferably, the filament 130 is biased towards a coiled configuration, such as that shown in FIG. 6, yet may be deformed into a generally linear configuration, such as that shown in FIG. 7. A first end 132 of the filament 130 is substantially permanently attached to the intermediate region 120, e.g., by bonding or welding, similar to the previous embodiment. Preferably, the first end 132 is attached within or adjacent to the slot 122, and a second end 133 of the filament 130 is loose.

In its unstressed or relaxed state, the filament 130 includes a first segment 134 that extends from the first end 132 transversely, and preferably substantially perpendicularly, to the longitudinal axis 119. The filament 130 also includes a second segment 136 that extends transversely from the first segment 134, and preferably substantially perpendicularly to the first segment 134. More preferably, the second segment 136 is biased to define a planar configuration, e.g., in the shape of a coil, as shown in FIG. 6. The planar configuration generally defines a plane that extends substantially parallel to the longitudinal axis 119 of the needle 114.

Alternatively, the second segment 136 may be biased towards other configurations instead of a coil that generally define a plane. For example, at least a portion of the second segment 136 may be biased towards a generally "L," "U," "Y," and/or "S" shape lying within the plane.

Turning to FIG. 7, the delivery apparatus 150 generally includes a sheath or outer member 152, and an inner pusher member 154. The sheath 152 generally is an elongate tubular member including a proximal end (not shown), a distal end 156, and a lumen 158 extending therebetween. The distal end 156 preferably has a size and shape for facilitating insertion into and along a blood vessel or other body lumen (not shown). The lumen 158 has a size for receiving the needle 114 therein, preferably such that the first end 116 is disposed distally to the second end 118, as shown.

The pusher member 154 is slidably disposed within the lumen 158, and includes a distal end 160 that is disposed proximate the second end 118 of the needle 114. The pusher member 154 may be movable axially relative to the sheath 152 for ejecting the needle 114 distally from the lumen 158. The pusher member 154 includes a gripping mechanism (not shown) for releasably securing the loose end (also not shown in FIG. 7) of the filament 130. The gripping mechanism may retrain the filament 130 in the generally linear configuration, as shown in FIG. 7. The gripping mechanism may include a clamp (not shown) that may be slidably received in or otherwise coupled to the pusher member 154. The clamp may be opened to receive the loose end of the filament, closed to secure the filament thereto, and-then opened again to release the filament, as explained further below. Alternatively, the filament may be directed into a slot (not shown) in the pusher member and secured within the slot by a coaxial member (also not shown) disposed within or around the pusher member 154.

An actuator (not shown) may be provided on the proximal end of the pusher member 154 and/or the sheath 152 for controlling or activating movement of the pusher member 154 relative to the sheath 152. In addition or alternatively, the actuator may be activated for releasing the loose end of the filament 130.

In addition, an imaging element, such as an IVUS (not shown), may be associated with the distal end 156 of the tubular member 152 for imaging beyond the distal end 156 of the tubular member 152 during a procedure, similar to the previous embodiment.

Figure 8A:
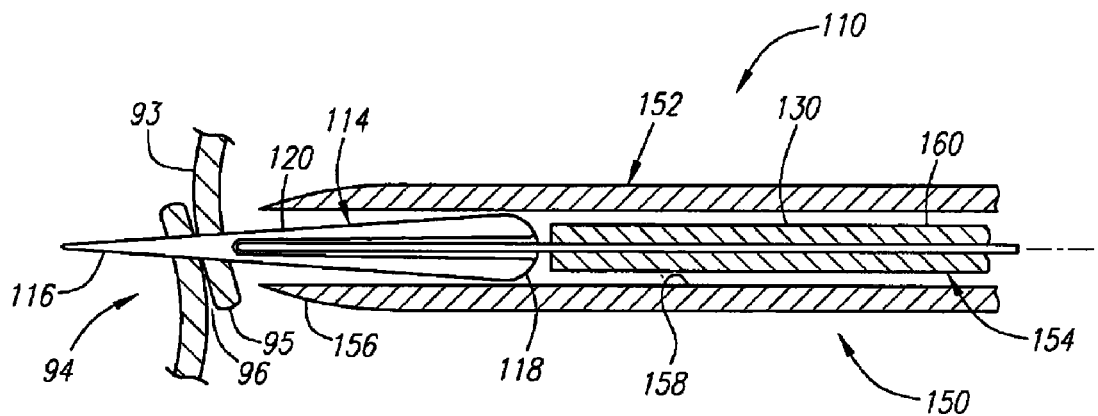
FIGS. 8A and 8B are cross-sectional views, showing a method for closing a PFO using the needle apparatus of FIG. 6.
Figure 8B:
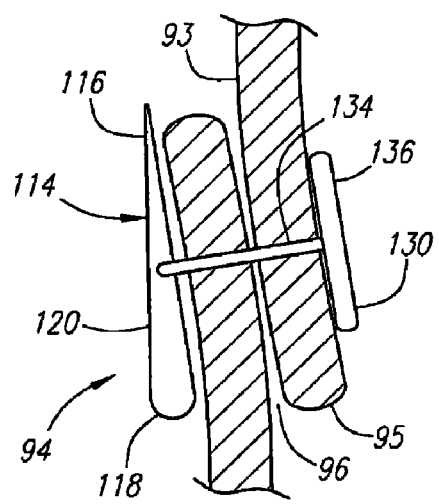

Turning to FIGS. 8A and 8B, the apparatus 110 may be used to close and/or seal a septal defect 94 within a patient's heart (not shown). Generally, the septal defect 94 includes a flap of tissue 95 partially detached from a septum wall 93 between first and second chambers of the heart, such as a PFO or PDA as described above, such that the flap of tissue 95 and surrounding tissue define a septal opening 96 through the septum wall 93.

Initially, a needle 114 may be provided that includes a first end 116 defining a tissue-penetrating tip, a second end 118 defining a substantially blunt tip, and an intermediate portion 120 between the first and second ends 116, 118 from which a filament 130 extends. The needle 114 may be disposed within a lumen 158 or otherwise carried by a sheath 152. Preferably, the filament 130 is secured to a pusher member 154, the distal end 160 of which is disposed adjacent the second end 118 of the needle 114.

The needle 114, e.g., within the sheath 152, may be advanced through the patient's vasculature until the needle 114 is disposed within the first chamber of the heart, e.g., adjacent the septal opening 96. The first end 116 of the needle 114 may be inserted through the flap of tissue 95, as shown in FIG. 8A, until the second end 118 passes through the flap of tissue 95 and an overlapping portion of the septum wall 93. Preferably, the pusher member 154 is advanced against the second end 118 of the needle, thereby directing the needle 114 entirely through the septum wall 93 until the needle 114 is disposed within the second chamber of the heart.

The filament 130 may then be pulled proximally, thereby causing the needle 114 to pivot about the intermediate region 120 such that the needle 114 extends substantially parallel to the septum wall 93. The first and second ends 116, 118 of the needle 114 may straddle the septal opening 95 within the second chamber, similar to the previous embodiment, or otherwise draw the flap of tissue 95 against the septum wall 93.

The filament 130 may then be released from the pusher member 154, and the sheath 152 and pusher member 152 removed from the patient.

Once the second end of the filament 114 is released, because of its inherent bias, the filament 130 may resiliently assume a generally planar configuration, thereby engaging the flap of tissue 95 and/or the septum wall 93 between the needle 114 and the filament 130. Preferably, a first segment 134 of the filament 130 extends transversely from the needle 114, i.e., through the flap of tissue 95 and septum wall 95. A second segment 136 of the filament 130 assumes a planar configuration against the flap of tissue 95 to at least partially close the septal opening 95, as shown in FIG. 8B.

Preferably, as explained above, the filament 130 may assume a coiled configuration defining a plane that is generally parallel with the septum wall 93. The filament 130 in the coiled configuration may have sufficient width to engaging tissue surrounding the opening 96. Alternatively, the filament 130 may simply retain the needle 114 against the flap of tissue 95, thereby maintaining the flap of tissue 95 against the septum wall 93 to substantially close and/or seal the opening 96.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for treating a patent foramen ovale, comprising:
    advancing an implantable device through the vasculature of a subject and into a first atrial chamber of the heart, wherein the atrial septal wall of the heart has a patent foramen ovale characterized by a first tissue flap and a second tissue flap, at least a portion of the first tissue flap overlapping at least a portion of the second tissue flap to define a tunnel therebetween; and
    situating the implantable device within a first piercing in the portion of the first tissue flap overlapping the second tissue flap and within a second piercing in the portion of the second tissue flap, wherein situating the implantable device comprises engaging the first tissue flap with a first portion of the implantable device in a second atrial chamber of the heart and then engaging the second tissue flap with a second portion of the implantable device in the first atrial chamber of the heart, wherein the first and second tissue flaps are engaged such that the first tissue flap is held in contact with the second tissue flap to close the tunnel.

2. The method of claim 1, further comprising externally or internally imaging the implantable device.

3. The method of claim 2, wherein the implantable device comprises a radiopaque marker and wherein imaging the implantable device comprises externally imaging the radiopaque marker with fluoroscopy.

4. The method of claim 1, wherein advancing the implantable device through the vasculature of a subject comprises advancing the implantable device through the vasculature while the implantable device is within an elongate delivery apparatus.

5. The method of claim 1, wherein the implantable device further comprises an intermediate portion between the first portion and the second portion.

6. The method of claim 5, wherein the first portion of the implantable device is an elongate portion coupled with the intermediate portion of the implantable device such that the elongate portion is pivotable between a first configuration suitable for housing within the delivery apparatus and the retaining configuration.

7. The method of claim 6, wherein the first portion of the implantable device further comprises a first end configured to pass through tissue, a second end, and an intermediate region located therebetween.

8. The method of claim 6, wherein the first portion of the implantable device further comprises a first end configured to penetrate tissue, a second end, and an intermediate region located therebetween.

9. The method of claim 8, wherein the intermediate region of the first portion is pivotally coupled with the intermediate portion of the implantable device.

10. The method of claim 1, wherein situating the implantable device comprises securing the second portion to the implantable device in a configuration configured to retain the second portion against the second tissue flap.

11. The method of claim 1, wherein the first portion engages the first tissue flap in a retaining configuration where a longitudinal axis of the first portion lies substantially perpendicular to a longitudinal axis of the portion of the implantable device within the first piercing.

12. The method of claim 11, wherein the first portion is an elongate portion.

13. The method of claim 11, wherein the first portion is an elongate, needle-like portion.

14. The method of claim 1, wherein the first portion comprises a laterally extending member configured to engage the first tissue flap and the second portion comprises a laterally extending member configured to engage the second tissue flap.

15. The method of claim 1, wherein engaging the first tissue flap with the first portion of the implantable device comprises transitioning the first portion of the implantable device to a retaining configuration configured to retain the first portion against the first tissue flap.

16. The method of claim 1, wherein the second portion of the implantable device comprises retaining arms configured to engage the second tissue flap.

17. The method of claim 1, wherein the second portion of the implantable device comprises at least one laterally extending member configured to engage the second tissue flap.

18. The method of claim 1, wherein the second portion of the implantable device comprises a plurality of laterally extending members configured to engage the second tissue flap.

19. The method of claim 1, wherein engaging the second tissue flap with the second portion of the implantable device comprises allowing the second portion of the implantable device to transition to a retaining configuration configured to retain the second portion against the second tissue flap.

20. The method of claim 19, wherein the second portion of the implantable device is biased towards the retaining configuration.

21. The method of claim 20, wherein the retaining configuration lies substantially in a plane parallel to the second tissue flap.

22. The method of claim 21, wherein the retaining configuration is generally coiled.

23. The method of claim 21, wherein the retaining configuration is a generally "L" shape.

24. The method of claim 21, wherein the retaining configuration is a generally "U" shape.

25. The method of claim 21, wherein the retaining configuration is a generally "Y" shape.

26. The method of claim 21, wherein the retaining configuration is a generally "S" shape.

27. The method of claim 1, wherein the first portion of the implantable device engages a first septal surface exposed within a second atrial chamber.

28. The method of claim 1, wherein the second portion of the implantable device engages a second septal surface exposed within the first atrial chamber.

29. The method of claim 1, wherein the first atrial chamber is the right atrium and the second atrial chamber is the left atrium.

30. The method of claim 1, wherein the first atrial chamber is the left atrium and the second atrial chamber is the right atrium.

31. The method of claim 30, wherein advancing the implantable device through the vasculature of the subject comprises advancing the implantable device through the vena cava to the heart.

32. The method of claim 1, wherein the first portion of the implantable device comprises a tip configured to pass through tissue.

33. The method of claim 1, wherein the first portion of the implantable device comprises a tip configured to penetrate tissue.

34. The method of claim 33, wherein situating the implantable device comprises advancing the first portion of the implantable device through the second tissue flap to create the second piercing.

35. The method of claim 34, wherein situating the implantable device comprises advancing the implantable device through the first tissue flap to create the first piercing.

36. The method of claim 35, wherein situating the implantable device further comprises advancing the implantable device until the first portion of the implantable device is fully exposed within the second atrial chamber.

37. The method of claim 36, wherein situating the implantable device comprises transitioning the first portion of the implantable device to a retaining configuration configured to retain the implantable device against the first tissue flap.

38. The method of claim 37, wherein situating the implantable device comprises allowing the second portion of the implantable device to transition to a retaining configuration to retain the second portion against the second tissue flap.

39. The method of claim 37, wherein situating the implantable device comprises coupling the second portion with the implantable device in a configuration configured to retain the second portion against the second tissue flap.

40. The method of claim 39, wherein the second portion is a locking element.

41. The method of claim 40, wherein the locking element comprises arms.

42. The method of claim 40, wherein the implantable device comprises a filament and wherein the locking element is configured to lockingly engage the filament.

43. The method of claim 42, wherein the filament is a suture.

44. The method of claim 37, wherein the first portion of the implantable device resides substantially flat against the first tissue flap in the retaining configuration.

45. The method of claim 44, wherein the implantable device further comprises an intermediate portion between the first portion and the second portion.

46. The method of claim 45, wherein the first portion of the implantable device is an elongate portion coupled with the intermediate portion of the implantable device.

47. The method of claim 46, wherein situating further comprises pivoting the elongate portion from a first configuration suitable for housing within a delivery apparatus to the retaining configuration.

48. The method of claim 47, wherein the first portion of the implantable device further comprises a first end configured to penetrate tissue, a second end, and an intermediate region located therebetween.

49. The method of claim 48, wherein the intermediate region is coupled with the intermediate portion of the implantable device.

50. The method of claim 1, wherein the implantable device comprises NITINOL.

51. The method of claim 1, wherein the implantable device comprises stainless steel.

52. The method of claim 1, wherein the implantable device comprises a shape memory material.

53. The method of claim 1, wherein advancing the implantable device through the vasculature comprises advancing an elongate tubular member having a lumen through the vasculature with the implantable device housed within the lumen.

54. The method of claim 53, wherein the implantable device comprises a radiopaque marker.

55. The method of claim 53, wherein the tubular member comprises a radiopaque marker.

56. The method of claim 53, wherein situating the implantable device comprises advancing the implantable device through a distal end of the tubular member with a distal end of an elongate pusher member.

57. The method of claim 56, wherein the pusher member comprises a radiopaque marker.

58. The method of claim 56, wherein situating the implantable device further comprises:
    advancing the first portion of the implantable device through the first and second tissue flaps with the pusher member; and
    transitioning the first portion of the implantable device to a retaining configuration after the first portion has been advanced through the first and second tissue flaps.

59. The method of claim 58, wherein the first portion of the implantable device comprises a tip configured to penetrate tissue.

60. The method of claim 58, wherein situating the implantable device further comprises allowing the second portion of the implantable device to transition to a retaining configuration after the second portion exits the distal end of the tubular member.

61. The method of claim 56, further comprising advancing the pusher member with an actuator.

62. The method of claim 61, wherein the elongate tubular member has a substantially atraumatic distal tip.

63. The method of claim 62, wherein the distal end of the pusher member is configured to engage the implantable device.

64. The method of claim 63, wherein the pusher member comprises a gripping mechanism for gripping the implantable device.

65. The method of claim 1, wherein advancing the implantable device through the vasculature of the subject comprises advancing the implantable device through an artery.

66. The method of claim 1, wherein situating the implantable device comprises advancing a sharp end of the implantable device through the first tissue flap to create the first piercing.

67. The method of claim 66, wherein situating the implantable device comprises advancing the sharp end of the implantable device through the second tissue flap to create the second piercing.

68. The method of claim 67, wherein situating the implantable device comprises releasing the implantable device while located within the first and second piercings.

69. The method of claim 1, wherein situating the implantable device comprises releasing the implantable device while located within the first and second piercings.

* * * * *